(12) United States Patent
Kanagawa et al.

(10) Patent No.: US 8,447,088 B2
(45) Date of Patent: May 21, 2013

(54) X-RAY IMAGING SYSTEM, X-RAY IMAGING METHOD, AND COMPUTER-READABLE MEDIUM STORING X-RAY IMAGING PROGRAM

(75) Inventors: Eiichi Kanagawa, Kanagawa (JP); Noriaki Ida, Kanagawa (JP); Sadato Akahori, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 416 days.

(21) Appl. No.: 12/923,422

(22) Filed: Sep. 21, 2010

(65) Prior Publication Data

US 2011/0075908 A1 Mar. 31, 2011

(30) Foreign Application Priority Data

Sep. 29, 2009 (JP) .................... 2009-224017

(51) Int. Cl.
*G06K 9/00* (2006.01)
*G06K 9/38* (2006.01)

(52) U.S. Cl.
USPC .................. 382/131; 382/270; 378/4; 378/98

(58) Field of Classification Search
USPC ................ 382/131, 270; 378/4, 98
See application file for complete search history.

(56) References Cited

U.S. PATENT DOCUMENTS

| 5,165,100 A * | 11/1992 | Hsieh et al. ................ 382/131 |
| 5,875,040 A * | 2/1999 | Matraszek et al. ............ 358/453 |
| 6,333,963 B1 | 12/2001 | Kaifu et al. |
| 6,556,720 B1 * | 4/2003 | Avinash ...................... 382/260 |
| 6,663,281 B2 * | 12/2003 | Aufrichtig et al. ........... 378/207 |
| 6,738,501 B2 * | 5/2004 | Ma et al. ..................... 382/131 |
| 7,218,705 B2 * | 5/2007 | Xue et al. .................... 378/98.8 |
| 7,839,975 B2 * | 11/2010 | Nakamura et al. ............. 378/95 |
| 7,881,514 B2 * | 2/2011 | Oaknin et al. ............... 382/128 |
| 2006/0050847 A1 * | 3/2006 | Jaffray et al. ................. 378/65 |
| 2006/0274145 A1 * | 12/2006 | Reiner .......................... 348/62 |
| 2006/0291624 A1 | 12/2006 | Xue et al. |
| 2008/0012967 A1 * | 1/2008 | Kuwabara .................... 348/246 |
| 2009/0080764 A1 * | 3/2009 | Srinivasan et al. ........... 382/150 |
| 2009/0218480 A1 * | 9/2009 | Srinivasan et al. ......... 250/252.1 |
| 2010/0054400 A1 * | 3/2010 | Ren et al. ....................... 378/37 |

(Continued)

FOREIGN PATENT DOCUMENTS

| JP | 10-327317 | 12/1998 |
| JP | 2007-000632 | 1/2007 |

*Primary Examiner* — Matthew Bella
*Assistant Examiner* — Patrick Edwards
(74) *Attorney, Agent, or Firm* — Jean C. Edwards, Esq.; Edwards Neils PLLC

(57) ABSTRACT

An X-ray imaging system comprises: an imaging unit for irradiating a subject with X ray at different angles while moving an X-ray source in one direction in tomosynthesis imaging, detecting the X ray with which the subject has been irradiated with a flat panel detector to acquire projection data of X-ray images taken at different angles; and an image processor for reconstructing a first X-ray tomographic image using projection data acquired by the imaging unit, the image processor including: a correction decision unit for selecting, according to a given selection condition, one of previously provided different corrections to be performed on the projection data; a first image correction unit for performing correction based upon the correction selected by the correction decision unit on the projection data; and a first image reconstruction unit for reconstructing the first X-ray tomographic image using the corrected projection data.

14 Claims, 3 Drawing Sheets

U.S. PATENT DOCUMENTS

2010/0246913 A1* 9/2010 Srinivas et al. ............... 382/131
2011/0075908 A1* 3/2011 Kanagawa et al. ........... 382/131
2011/0075909 A1* 3/2011 Kanagawa et al. ........... 382/131
2011/0075910 A1* 3/2011 Kanagawa et al. ........... 382/131

* cited by examiner

X-RAY IMAGING SYSTEM, X-RAY IMAGING METHOD, AND COMPUTER-READABLE MEDIUM STORING X-RAY IMAGING PROGRAM

CROSS-REFERENCE TO RELATED APPLICATIONS

The present application claims priority from Japanese Patent Application No. 2009-224017, filed Sep. 29, 2009, the contents of which are herein incorporated by reference in their entirety.

BACKGROUND OF THE INVENTION

The present invention relates to an x-ray imaging system, an x-ray imaging method, and a computer-readable medium storing an x-ray imaging program for reconstructing an X-ray tomographic image of a subject at a given height thereof using projection data of X-ray images acquired by tomosynthesis imaging.

An X-ray imaging system for tomosynthesis imaging irradiates a subject with X ray at different angles while moving an X-ray source in one direction and detects the X ray with which the subject has been irradiated with a flat panel X-ray detector (FPD) to achieve acquisition of projection data corresponding to X-ray images of the subject taken at different angles by a single imaging operation. Then the process proceeds to image processing using the projection data corresponding to the X-ray images to reconstruct an X-ray tomographic image at a cross section of the subject at a given height thereof.

Now, reconstruction of an X-ray tomographic image will be described.

In tomosynthesis imaging, the X-ray source is moved in one direction to irradiate a subject 30 with X ray from positions S1, S2, and S3 as illustrated in FIG. 3A, so that two objects A, B are projected onto different positions in X-ray images (projection data) P1, P2, and P3 of the subject 30.

In the X-ray image P1, for example, the X-ray source, located in the position S1 to the left of the objects A, B in FIG. 3A, causes projections of the objects A, B to be formed in positions P1A, P1B that are set off to the right of the objects A, B. Likewise, in the X-ray image P2, the projections are formed in positions P2A, P2B that are substantially directly beneath the objects A, B; in the X-ray image P3, the projections are formed in positions P3A, P3B that are set off to the left of the objects A, B.

To reconstruct an X-ray tomographic image of the subject at a cross section located at a height of the object A, the X-ray image P1 is shifted leftward, and the X-ray image P3 is shifted rightward, for example, so that the projection positions P1A, P2A, and P3A coincide as illustrated in FIG. 3B (shift addition method). Thus, an X-ray tomographic image is reconstructed wherein the cross section located at the height of the object A is accentuated. An X-ray tomographic image at a cross section located at a given height, for example, at a height of the object B may likewise be reconstructed.

The FPD comprises photoelectric conversion elements arranged in matrix form and an X-ray receiving surface divided into sub-areas. The FPD has a data readout circuit in each sub-area. Therefore, to compensate for a variation in characteristics of photoelectric conversion elements, the data readout circuits or the like, various corrections are performed on projection data that are read out from the FPD.

JP 2007-632 A, for example, relates to compensation of an offset signal produced by a flat panel detector of a radiographic imaging apparatus. This literature describes an offset compensation for the flat panel detector using an offset map.

JP 10-327317 A, on the other hand, relates to a radiographic imaging apparatus capable of correcting an error contained in the imaging output caused by the difference between conditions under which data used for correction are obtained and conditions under which imaging is actually performed to provide image information having an enhanced signal-to-noise ratio.

Described in this literature is an imaging apparatus provided with an imaging means including photoelectric conversion elements one-dimensionally or two-dimensionally arranged, the imaging apparatus further comprising means for storing an imaging output in an imaging mode, means for storing imaging conditions in the imaging mode, means for obtaining a correction output in a correction mode operated using the stored imaging conditions, and correction means for correcting the imaging output using the correction output.

However, tomosynthesis imaging acquires projection data corresponding to a plurality of X-ray images, each of which has a large size, resulting in projection data having a large data quantity. Accordingly, where every image data having a large data quantity such as imaging data of X-ray images as acquired in tomosynthesis imaging was corrected, reconstruction of an X-ray tomographic image required a significantly long time.

Further, some corrections, the same as those used in plain X-ray imaging, do not produce great effects upon the image quality of tomographic images whereas a number of other corrections are only effective when used in tomosynthesis imaging. Thus, while changing corrections according to imaging conditions, image data and requirements of users is effective, the inventions described in JP 2007-632 A and JP 10-327317 A were not so configured as to permit switching between corrections or selection of one of the corrections according to the conditions as described above.

SUMMARY OF THE INVENTION

An object of the present invention is to solve the above problems associated with the prior art and provide an x-ray imaging system, an x-ray imaging method, and a computer-readable medium storing an x-ray imaging program capable of reconstructing an X-ray tomographic image by performing a correction suitable for a required image quality of the X-ray tomographic image on X-ray images acquired by tomosynthesis imaging.

An X-ray imaging system according to the present invention comprises:

an imaging unit for irradiating a subject with X ray at different angles while moving an X-ray source in one direction in tomosynthesis imaging, detecting the X ray with which the subject has been irradiated with a flat panel detector to acquire projection data of X-ray images taken at different angles; and an image processor for reconstructing a first X-ray tomographic image using projection data of the X-ray images acquired by the imaging unit, the image processor including:

a correction decision unit for selecting, according to a given selection condition, one of previously provided different corrections to be performed on the projection data of the X-ray images acquired by the imaging unit;

a first image correction unit for performing correction based upon the correction selected by the correction decision unit on the projection data of the X-ray images acquired by the imaging unit; and a first image reconstruction unit for reconstructing the first X-ray tomographic image using the projection data of the X-ray images corrected by the first image correction decision unit.

An X-ray imaging method according to the present invention comprises the steps of:

irradiating a subject with X ray at different angles while moving an X-ray source in one direction in tomosynthesis imaging, and detecting the X ray with which the subject has been irradiated with a flat panel detector to acquire projection data of X-ray images taken at different angles;

selecting, according to a given selection condition, one of previously provided different corrections to be performed on the projection data of the acquired X-ray images;

performing a first correction based upon the selected correction on the projection data of the acquired X-ray images; and reconstructing a first X-ray tomographic image using the projection data of the X-ray images corrected according to the first correction.

A computer-readable medium storing an X-ray imaging program for causing a computer to execute the steps of:

irradiating a subject with at different angles while moving an X-ray source in one direction in tomosynthesis imaging, and detecting the X ray with which the subject has been irradiated with a flat panel detector to acquire projection data of X-ray images taken at different angles;

selecting, according to a given selection condition, one of previously provided different corrections to be performed on the projection data of the acquired X-ray images;

performing a first correction based upon the selected correction on the projection data of the acquired X-ray images; and reconstructing a first X-ray tomographic image using the projection data of the X-ray images corrected according to the first correction.

DETAILED DESCRIPTION OF THE INVENTION

The X-ray imaging system, X-ray imaging method, and X-ray imaging program of the invention will be described in detail referring to the attached drawings of preferred embodiments.

Figure 1:
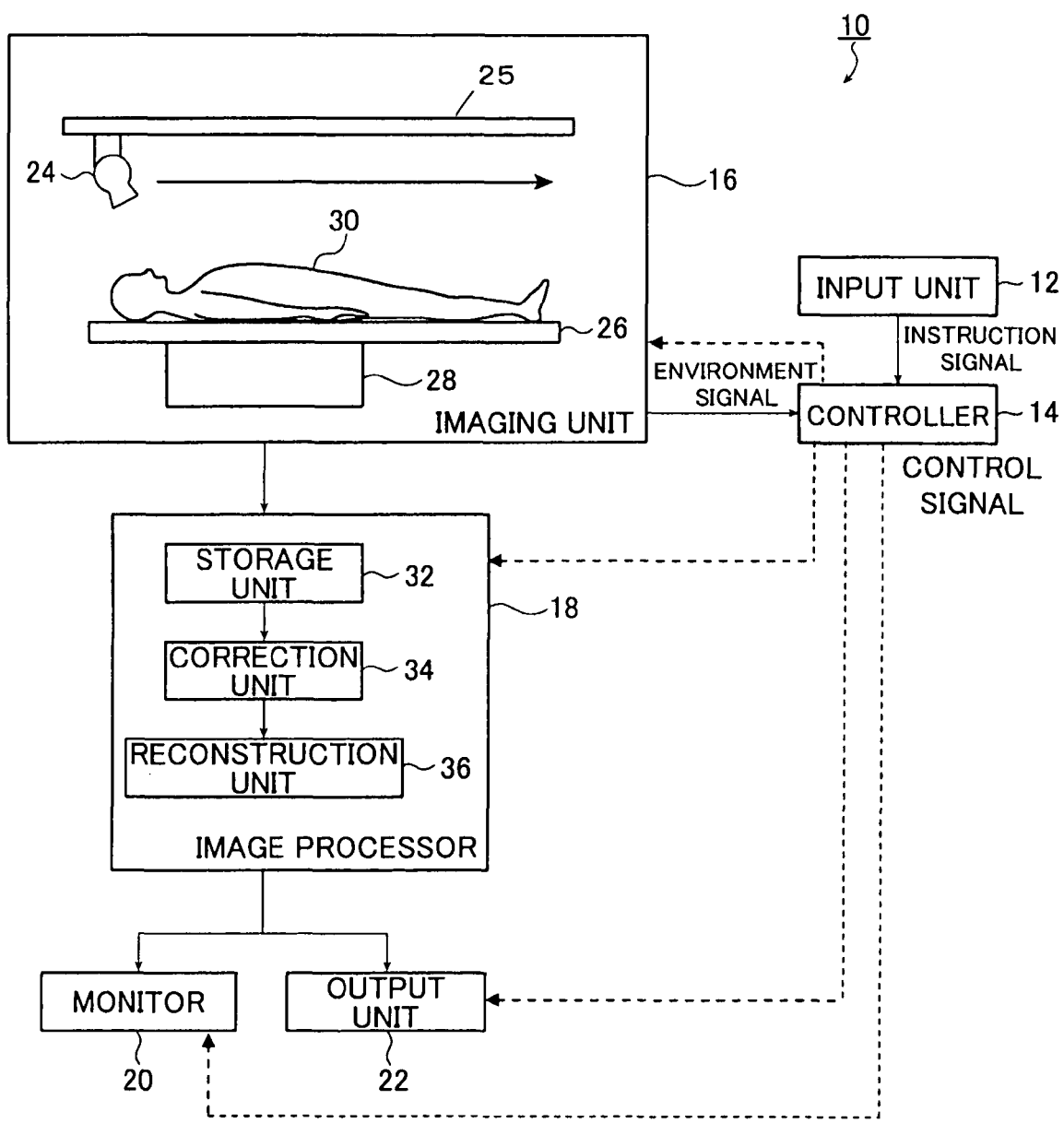
FIG. 1 is a block diagram representing a configuration of a radiographic imaging system according to an embodiment of the invention.

FIG. 1 is a block diagram representing a configuration of an X-ray imaging system 10 according to an embodiment of the invention. The X-ray imaging system 10 acquires images of a subject 30 such as a human body by tomosynthesis imaging (X-ray imaging) and reconstructs an X-ray tomographic image at a cross section located at a given height of the subject 30. The imaging system 10 comprises an input unit 12, a controller 14, an imaging unit 16, an image processor 18, a monitor 20, and an output unit 22.

The input unit 12 is provided to enter various instructions including but not limited to an instruction to start imaging, an instruction for imaging conditions described later, and an instruction to switch operations and may be configured by a mouse, a keyboard, etc. The input unit 12 produces an instruction signal, which is received by the controller 14.

The controller 14 produces control signals according to an instruction signal transmitted from the input unit 12 and an environment signal transmitted from the imaging unit 16 to control the operations of the imaging system 10 including imaging operations by the imaging unit 16, image processing by the image processor 18, screen display by the monitor 20, and output processing by the output unit 22. The controller 14 produces control signals respectively for the imaging unit 16, the image processor 18, the monitor 20, and the output unit 22.

The environment signal indicates an imaging environment of the imaging unit 16 when images are acquired. The environment signal will be described later in detail.

The imaging unit 16 acquires images of the subject 30 by tomosynthesis imaging according to a control signal supplied from the controller 14, and comprises an X-ray source 24, a carrier 25 for moving the X-ray source 24, an imaging table 26, and a flat panel type X-ray detector (FPD) 28.

The X-ray source 24 is disposed at a higher position than the subject 30 located on the top surface of the imaging table 26. The carrier 25 moves the X-ray source 24 parallel to the top surface of the imaging table 26.

The FPD 28 is disposed on the bottom side of the imaging table 26 so that its X-ray receiving surface faces upwards. The FPD 28 detects incoming X-ray passing through the subject 30 and effects photoelectric conversion to produce digital image data (projection data) corresponding to an acquired X-ray image of the subject 30. Accordingly, the FPD 28 used in the invention may be a direct type whereby radiation is directly converted into an electric charge, an indirect type whereby radiation is temporarily converted into light, which is then converted into an electric signal, or any of various other types. The FPD 28 may be configured so that it is movable in the same direction as the X-ray source 24.

In tomosynthesis imaging, the carrier 25 controls the movement of the X-ray source 24 to move the X-ray source 24 in one direction and change the X-ray irradiation angle toward the subject 30 so as to irradiate the subject 30 with X ray at different imaging angles (at given time intervals). The X-ray radiated by the X-ray source 24 passes through the subject 30 to be incident on the light receiving surface of the FPD 28, and is detected and converted into electricity by the FPD 28 so that projection data corresponding to the acquired X-ray image of the subject 30 is obtained.

In tomosynthesis imaging, acquired are a plurality of X-ray images, for example 20 to 80 images, of the subject 30, each taken at different imaging angles, with a single imaging operation, whereupon the FPD 28 sequentially outputs projection data corresponding to the acquired X-ray images.

The image processor 18 receives the projection data of the X-ray images acquired by the imaging unit 16 according to the control signal supplied from the controller 14 and performs image processing (including correction and image synthesis) using the projection data of the X-ray images to reconstruct an X-ray tomographic image of the subject 30 at a cross section thereof located at a given height. The image processor 18 comprises a storage unit 32, a correction unit 34, and a reconstruction unit 36.

The storage unit 32 stores the projection data of the X-ray images acquired by the imaging unit 16. The correction unit 34 performs a given correction of the projection data of the X-ray images stored in the storage unit 32. The reconstruction unit 36 uses the projection data of the X-ray images corrected by the correction unit 34 to perform image synthesis, thus reconstructing an X-ray tomographic image of the subject 30 at a cross section thereof at a given height.

The image processor 18 may be configured by hardware (a device) or a program for causing a computer to execute a part of the X-ray image processing method of the invention. The program may be stored in a computer-readable medium.

The monitor 20 displays an X-ray tomographic image reconstructed by the image processor 18 according to the control signal supplied from the controller 14 and may be configured for example by a flat panel display such as a liquid crystal display.

The output unit 22 outputs an X-ray tomographic image reconstructed by the image processor 18 according to the control signal supplied from the controller 14 and may be configured by, for example, a thermal printer for printing out the X-ray tomographic image and a storage device capable of storing digital image data of the X-ray tomographic image in any of various recording media.

Next, the image processor 18 will be described in further detail.

Figure 2:
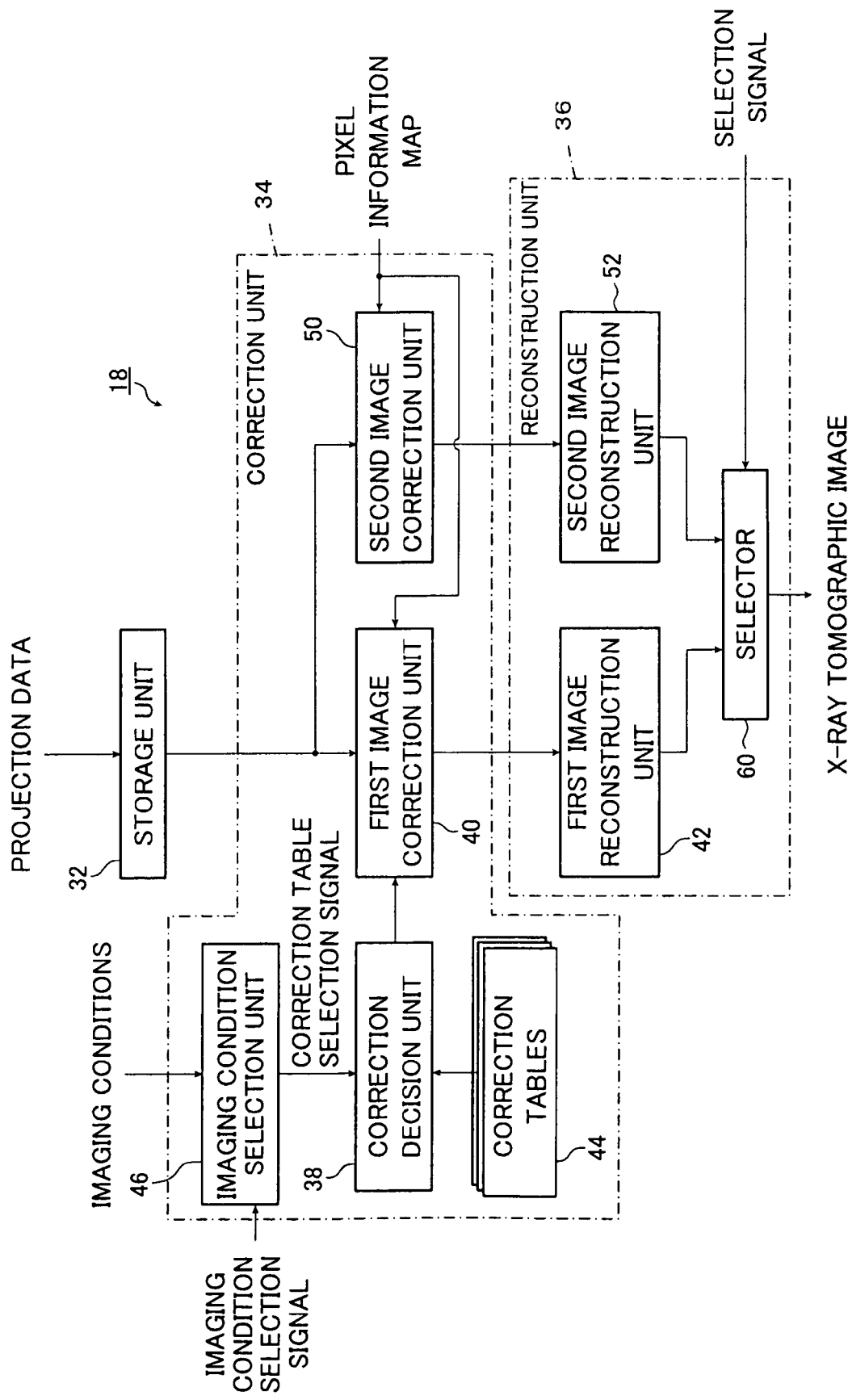
FIG. 2 is a block diagram representing a configuration of an image processor of the radiographic imaging system illustrated in FIG. 1.
Figure 3A:
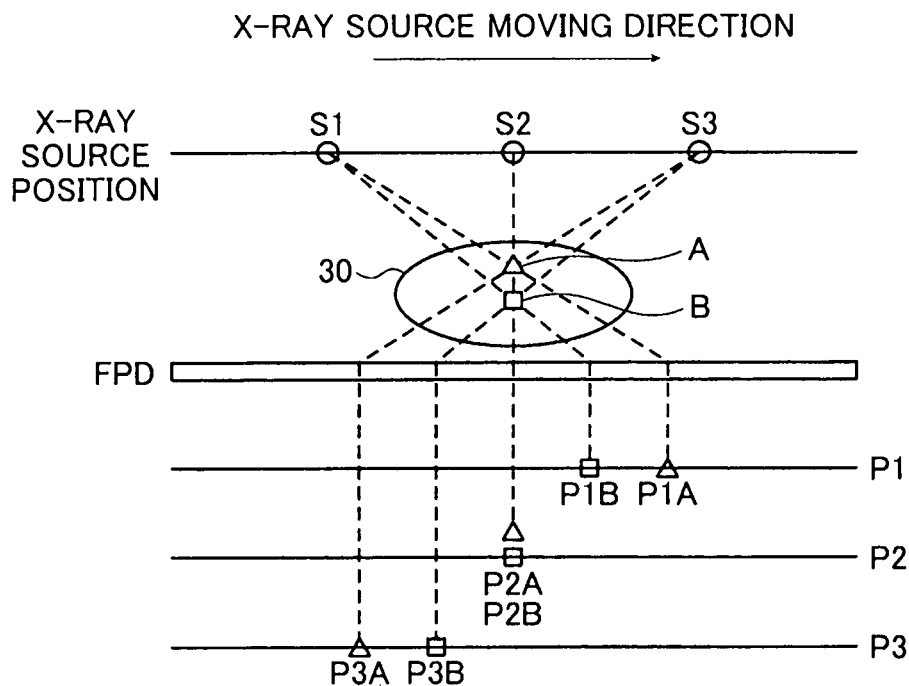
FIGS. 3A and 3B are conceptual views illustrating reconstruction of an X-ray tomographic image in tomosynthesis imaging.
Figure 3B:
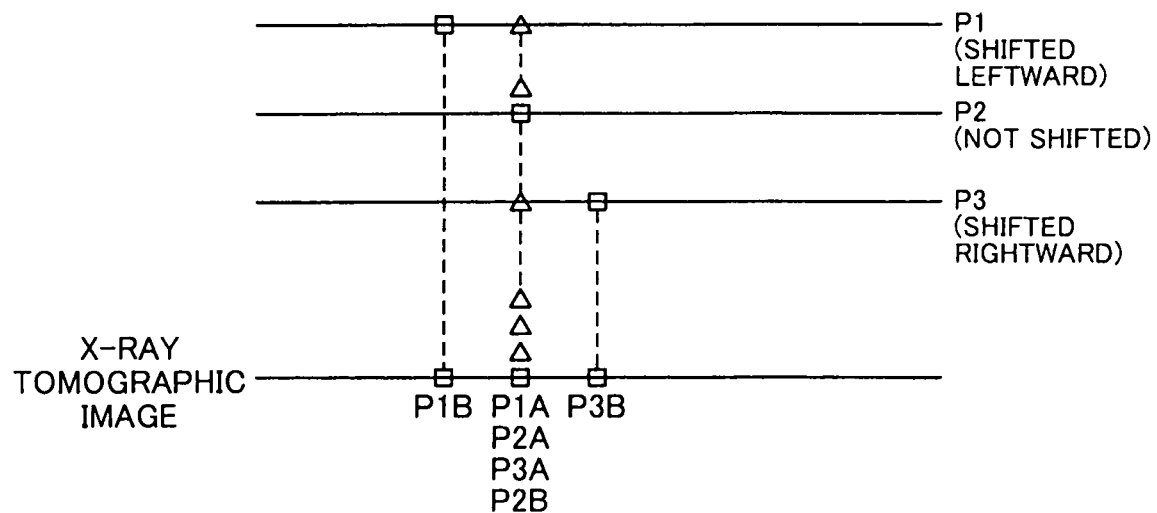

FIG. 2 is a block diagram illustrating a detailed configuration of the image processor 18 of FIG. 1. The image processor 18 comprises the storage unit 32, a correction decision unit 38, first and second image correction units 40, 50, first and second image reconstruction units 42, 52, correction tables 44, an imaging condition selection unit 46, and a selector 60. The correction decision unit 38, the first and the second image correction units 40, 50, the correction tables 44, and the imaging condition selection unit 46 constitute the correction unit 34. The first and the second image reconstruction units 42, 52 and the selector 60 constitute the reconstruction unit 36.

The imaging condition selection unit 46 selects one or more imaging conditions from among previously provided tomosynthesis imaging conditions according to an imaging condition selection signal (control signal) supplied from the controller 14, and outputs a correction table selection signal for selecting a correction table 44 corresponding to the selected one or more imaging conditions.

The imaging conditions are stored for example in the controller 14 and transmitted from the controller 14 to the imaging condition selection unit 46. The imaging conditions will be described later in detail.

The imaging condition selection signal is a control signal for selecting one or more imaging conditions from a plurality of imaging conditions, and the correction table selection signal is used to select one correction table 44 from a plurality of correction tables 44.

The correction decision unit 38 selects one correction table 44 from a plurality of correction tables 44 each setting out one or more kinds of corrections according to the correction table selection signal supplied from the imaging condition selection unit 46, and selects a correction set out in a selected correction table 44 as a correction to be implemented on the projection data corresponding to the respective X-ray images acquired by the imaging unit 16.

The correction table 44 is in a one-to-one correspondence with the selection signal thereof and therefore can be uniquely selected according to the selection condition. The correction tables 44 are for example stored in the image processor 18.

Where a single correction table 44 contains two or more corrections, the order in which they are executed may be specified. The use of correction tables 44 is not essential, and the correction decision unit 38 may select a correction to be executed on the projection data of the X-ray images acquired by the imaging unit 16 from a plurality of previously provided corrections according to the correction selection signal supplied form the imaging condition selection unit 46.

The correction decision unit 38 may decide not to perform correction on the projection data of the X-ray images acquired by the imaging unit 16 according to the correction table selection signal or the correction selection signal.

Referring to an image information map, the first image correction unit 40 performs a correction selected by the correction decision unit 38 on the projection data corresponding to the X-ray images acquired by the imaging unit 16.

The pixel information map stores a pixel position information, defect information, faulty gain information, shading information, offset information, and residual image information related to the FPD 28. The pixel information map may be produced, for example, based on projection data of an X-ray image taken in the absence of the subject 30. The pixel information map is stored in, for example, the FPD or the controller 14.

The position information is information on pixel positions with respect to the entire FPD; the defect information is information on a pixel at which X-ray cannot be detected because of, for example, a problem in manufacturing technology; faulty gain information is information on a pixel incapable of outputting pixel data that is in proportion to the amount of received X-ray like, for example, a pixel having a different X-ray detection sensitivity as compared with other pixels; shading information is information on inconsistent density among pixels; offset information is information on the initial value of the output from each pixel obtained when the FPD is read without X-ray irradiation; and residual image information is information on residual time and residual amount of the effects of X-ray irradiation, in each pixel.

Only one pixel information map may be provided or a plurality of different pixel information maps may be provided to contain the defect information, faulty gain information, shading information, offset information, and the residual image information on each pixel.

The first image reconstruction unit 42 uses the projection data of the X-ray images corrected by the first correction unit 40 to perform image synthesis, thus reconstructing a first X-ray tomographic image.

The second image correction unit 50 performs predetermined correction, for example a plurality of different kinds of corrections for acquiring a highest image quality, on the projection data of the X-ray images acquired by the imaging unit 16.

The second image reconstruction unit 52 uses the projection data of the X-ray images corrected by the second image processor 50 to perform image synthesis, thus reconstructing a second X-ray tomographic image having a highest image quality.

The first X-ray tomographic image, which is reconstructed by performing correction suitable for a required image quality of the X-ray tomographic image on the X-ray images acquired by tomosynthesis imaging, can be reconstructed to an X-ray tomographic image having a desired image quality at a higher speed and, hence, within a shorter time period than the second X-ray tomographic image. The second X-ray tomographic image, which is reconstructed through a number of corrections for obtaining a highest image quality, is reconstructed taking a longer time than the first X-ray tomographic image.

The selector 60 switches between the first X-ray tomographic image and the second X-ray tomographic image at a given timing to output either of them as an X-ray tomographic image according to the selection signal (control signal) supplied from the controller 14.

The second image correction unit 50, the second image reconstruction unit 52, and the selector 60 are not essential components of the image processor 18. These components are preferably provided as necessary when the output of the second X-ray tomographic image is required.

The timing at which selection is made between the first X-ray tomographic image and the second X-ray tomographic image according to the selection signal is not limited in any manner, permitting use of various timings.

For example, the timing may be so set that the first X-ray tomographic image is outputted from the selector 60 after the first image reconstruction unit 42 completed reconstruction of the first X-ray tomographic image and the second X-ray tomographic image is outputted after the second image reconstruction unit 52 completed reconstruction of the second X-ray tomographic image. According to this method, the first X-ray tomographic image is first displayed on the monitor 20 at high speed for a short time period, then the second X-ray tomographic image having a high image quality is automatically (unconditionally) displayed on the monitor 20.

Alternatively, when a given time period has elapsed from the completion of reconstruction of the second X-ray tomographic image, a switch may be made from the first X-ray tomographic image to the second X-ray tomographic image for the selector 60 to output the selected X-ray tomographic image. According to this method, when two or more first X-ray tomographic images are successively displayed in a shorter time than a given time period, the second X-ray tomographic image is not displayed. When the user is interested in the first X-ray tomographic image to allow it to be displayed longer than a given time period, the second X-ray tomographic image is automatically displayed.

Alternatively, after a given time period elapsed from the completion of reconstruction of the second X-ray tomographic image, a switch may be made between the first X-ray tomographic image and the second X-ray tomographic image according to an instruction (switching instruction) given from the outside through the input unit 12 so that the selector 60 outputs the selected X-ray tomographic image. According to this method, the user is allowed to switch between the first X-ray tomographic image and the second X-ray tomographic image of any X-ray tomographic image at any timing desired to display the switched one.

Alternatively, upon completion of reconstruction of the first X-ray tomographic image by the first image reconstruction unit 42, the selector 60 may output the first X-ray tomographic image, and switching from a part of the second X-ray tomographic image to a corresponding part of the first X-ray tomographic image may be repeated real-time each time the part of the second X-ray tomographic image is reconstructed by the second image reconstruction unit 52 until the reconstruction of the second X-ray tomographic image is completed. According to this method, a switch is made from the first X-ray tomographic image to the second X-ray tomographic image for a given unit (the unit may be a pixel, a line of pixels, etc.) during reconstruction of the second X-ray tomographic image instead of making a switch from the first X-ray tomographic image to the second X-ray tomographic image after the completion of reconstruction of the second X-ray tomographic image. Thus, a high image quality X-ray tomographic image can be displayed by unit in order of reconstruction.

Now, the imaging conditions will be described. The imaging conditions include, for example, the number of images to be acquired, the imaging angle, the imaging intervals, the dose of radiation, the purpose of image acquisition, the imaging situation, the site of the subject to be imaged, and the imaging range, all of which can be set (varied) by the user, and the imaging environment, which cannot be set by the user.

The number of images to be acquired is the number of X-ray images to be acquired during a single tomosynthesis imaging operation. The number of X-ray images acquired during a single tomosynthesis imaging operation is two or more without no upper limit, generally about 20 to 80 images are acquired.

The imaging angle is a variation (increment) in the angle at which the subject 30 is irradiated with X-ray emitted from the X-ray source 24 between tomosynthesis imaging operations whereby a plurality of X-ray images are acquired during a single imaging operation. The imaging angle is determined by the number of images to be acquired and a moving range (traveled distance) in the moving direction of the X-ray source 24.

The imaging interval is a time interval between shots in tomosynthesis imaging whereby a plurality of X-ray images are acquired during a single imaging operation. For example, when 50 images are acquired in 10 seconds, the interval will be 0.2 s/image. The imaging interval is determined by the number of images to be acquired and a moving range (traveled distance) in the moving direction of the X-ray source 24.

With the imaging system 10, when one of the number of images to be acquired, the imaging angle, and the imaging interval is determined, the other two factors are automatically determined, provided that the moving range of the X-ray source 24 in the moving direction is fixed.

The dose of radiation is a dose of X ray radiated by the X-ray source 24 for imaging, and is determined by the number of X-ray tubes, the tube voltage (kV), the tube current (mA), the imaging time (ms), tube current time (mAs), and the like.

The purpose of image acquisition is a purpose for which the reconstructed X-ray tomographic image is used. Specifically, the purpose of image acquisition may be to measure the length of a bone, diagnosis of a broken bone and a microfracture in a bone, etc.

The imaging situation is a length of time the situation allows for tomosynthesis imaging (time that can be used for tomosynthesis imaging). Cases of emergency, periodic health examinations, and thorough examinations are examples of the imaging situation.

The site of the subject to be imaged is a site of a human body to be imaged, and is exemplified by a lung, a chest, a breast, a lever, and an arm.

The imaging range is a range of a human body imaged by a single tomosynthesis imaging operation. The imaging range is exemplified by three different imaging ranges of large, medium, and small.

The imaging environment denotes conditions that cannot be changed by the user such as the type of the X-ray source 24, the type of the FPD 28, the temperature of the FPD 28 at the time of imaging, the type of the analog-to-digital converter circuit used in the FPD 28, the atmospheric temperature, the humidity, the atmospheric pressure, and the like.

The imaging conditions are not limited to the above examples and may include various conditions as appropriate such as the physique of the subject 30, the preferences of the user or the radiologist who interprets the X-ray images. Suppose, for example, that the number of images to be acquired is designated as an imaging condition, with 20, 40, and 80 provided for selection as the number of images to be acquired. Since a higher quality image is generally expected of X-ray tomographic images as the number of images to be acquired increases, the imaging condition selection unit 46 outputs a selection signal for selecting a correction table 44 that provides a correction that increases the image quality as the number of images to be acquired increases from, for example, 20, 40, to 80. The same applies to the imaging angle and the imaging interval.

As regards the dose of radiation, as the dose of radiation increases, for example, the selection signal outputted designates a correction table 44 for achieving an increased image quality.

As regards the purpose of image acquisition, the selection signal outputted designates a correction table 44 for achieving an image quality that increases as the purpose of image acquisition changes from, for example, measuring of a bone length, measuring of a large lesion to measuring of a small lesion in this order. When the purpose of image acquisition is measuring of a bone length, correction may be dispensed with.

As regards the imaging situation, the selection signal outputted designates a correction table 44 for achieving an image quality that increases as the imaging situation changes from, for example, emergency, a periodic health examination, to thorough examination in this order. When the imaging situation is a case of emergency, correction may be dispensed with.

As regards the site of the subject to be imaged, the selection signal outputted designates a correction table 44 for achieving an image quality that increases as the site of the subject to be imaged changes from, for example, an arm, a chest to breast in this order. When the site is a bone, correction may be dispensed with.

As regards the imaging range, as the imaging range decreases, for example, the selection signal outputted designates a correction table 44 for an increased image quality.

When the imaging environment is designated as an imaging condition, a selection signal is outputted for selecting a correction table 44 containing a correction corresponding to, for example, the type of the X-ray source 24 and the type of the FPD 28.

Specific items (such as the number of images for the number of images to be acquired) of imaging conditions and the relationship between each item and the image quality are not limited in any manner and may be set as desired.

Next, the correction by the image processor 18 will be described by way of offset correction, residual image correction, gain correction, defect correction, step correction, longitudinal inconsistent density correction, and a lateral inconsistent density correction.

Since the pixels of the FPD 28 have different characteristics, the pixel data that is outputted from the FPD 28 varies among the pixels even when the FPD 28 receives the same dose of X-ray. The offset correction corrects the difference in pixel data among the pixels of the FPD 28.

After acquisition of X-ray images, when the X-ray images are read out at short intervals, a residual image (remaining charge) of a previously acquired X-ray image might be read out. The residual image correction corrects the effects of residual image of a previously acquired X-ray image.

The gain correction corrects data corresponding to a pixel having a different X-ray detection sensitivity from those of other normal pixels and hence incapable of outputting pixel data proportional to the received X-ray dosage (faulty gain pixel).

The defective pixel correction corrects pixel data corresponding to a pixel (defective pixel) among those of the FPD 28 that cannot detect the X ray it receives and outputs pixel data that is fixed at all times to a certain value. The FPD 28 has an X-ray receiving surface divided into sub-areas, each of which has a data readout circuit. Since the circuits in the sub-areas have different characteristics, the pixel data that is outputted from the FPD 28 varies among the sub-areas even when the FPD 28 receives the same dose of X-ray. The step correction corrects the difference among the sub-areas (stepped density).

The longitudinal inconsistent density correction and the lateral inconsistent density correction correct longitudinal and lateral inconsistent densities that may occur in any location of the X-ray image.

The offset correction, residual image correction, gain correction, faulty pixel correction, step correction, longitudinal inconsistent density correction, and lateral inconsistent density correction are known corrections and may be implemented each using any of various methods including known methods. The corrections performed by the image processor 18 are not limited to the above specific examples and may include various other corrections.

As described above, all the X-ray images do not require the above corrections; some or many of the corrections are unnecessary or do not produce any effects upon the image quality of the reconstructed X-ray tomographic image depending upon the image quality desired, the site of the subject, and the like. For example, the faulty pixel correction and the step correction, requiring a long time, do not contribute greatly to improvement on image quality of a reconstructed X-ray tomographic image and, therefore, are preferably used selectively according to the relationship between the image quality required and the time needed for correction.

Next, the correction tables 44 will be described. In modes (1) to (5) of the correction tables 44 below, T1 is offset correction, T2 residual image correction, T3 gain correction, T4 faulty pixel correction, T5 step correction, T6 longitudinal inconsistent density correction, and T7 lateral inconsistent density correction.

(1) Low speed/high image quality mode: T1,T2,T3,T4,T5, T6,and T7.

(2) Medium speed/medium image quality mode: T1,T2, T3,and T4.

(3) High speed/low image quality mode: T1 and T3.

(4) Highest speed mode: no correction done.

(5) Manual setting mode: any desired correction is set from the outside.

For example, according to the low-speed/high image quality mode of the correction table 44, corrections T1, T2, T3, T4, T5, T6, and T7 are performed in this order. Likewise, according to the medium speed/medium image quality mode of the correction table 44, T1, T2, T3, and T4 are performed in this order, while according to the high speed/low image quality mode of the correction table 44, T1 and T3 are performed in this order.

According to the highest speed mode, the correction decision unit 38, instead of the correction tables 44, decides not to perform correction on the projection data of the X-ray images acquired by the imaging unit 16 in response to the selection signal. In this case, en empty correction table 44 (correction table 44 containing a correction whereby no correction is performed) may be used or no correction table 44 may be used.

The manual setting mode permits the user to set any correction desired from the outside using the input unit 12. The manual setting mode permits setting a correction unique to each hospital or other like institute, for example, and previously setting a correction according to radiologists' or doctors' preferences or a correction unique to each patient (file number). The modes (1) to (5) of the correction tables 44 above are given only by way of illustration, and the correction tables 44 may be each prepared as appropriate.

Next, the operation of the imaging system 10 in tomosynthesis imaging will be described.

The imaging unit 16 supplies the controller 14 with the environment signal indicating the imaging environment of the imaging unit 16 at the time of imaging. Controlled by the controller 14, the monitor 20 shows an input screen for entering instruction information on imaging conditions (information required to generate a control signal that is supplied to the imaging condition selection unit 46) using the input unit 12. Upon the user for the imaging system 10 entering imaging condition instruction information using the input unit 12, the controller 14 generates information on the imaging environment corresponding to the environment signal and a control signal corresponding to the entered imaging condition instruction information (imaging condition selection signal), which are in turn supplied to the imaging condition selection unit 46.

Then, the subject 30 is positioned on the top surface of the imaging table 26, whereupon the input unit 12 gives instruction to start imaging, thereby starting tomosynthesis imaging controlled by the controller 14.

Upon start of imaging, the imaging unit 16 irradiates the subject 30 with X ray as the carrier 25 moves the X-ray source 24 in one direction and changes the X-ray irradiation angle of the X-ray source 24 with respect to the subject 30 so that the subject 30 may be irradiated with X-ray at different imaging angles to acquire X-ray images taken at different imaging angles during a single imaging operation. Each time an X-ray image is acquired of the subject 30, the FPD 28 produces projection data corresponding to the X-ray image acquired.

The image processor 18 stores the projection data of the X-ray images acquired by the imaging unit 16 in the storage unit 32.

The imaging condition selection unit 46 selects one or more imaging conditions from among previously provided tomosynthesis imaging conditions according to a control signal, and outputs a selection signal of a correction table 44 corresponding to the selected one or more imaging conditions.

Subsequently, the correction decision unit 38 selects one correction table 44 from a plurality of correction tables 44 previously provided according to the correction table selection signal supplied from the imaging condition selection unit 46, and determines a correction set out in a selected correction table 44 as a correction to be implemented on the projection data corresponding to the respective X-ray images acquired by the imaging unit 16.

Then, the first image correction unit 40 performs correction determined by the correction decision unit 38 on the projection data of the X-ray images stored in the storage unit 32, and the first image reconstruction unit 42 uses the projection data corresponding to the X-ray images corrected by the first image correction unit 40 to reconstruct the first X-ray tomographic image at a cross section located at a given height of the subject 30.

Concurrently with the reconstruction processing by the first X-ray tomographic image, the second image correction unit 50 performs a given correction for obtaining an X-ray tomographic image having a highest image quality on the projection data of the X-ray images stored in the storage unit 32, and the second image reconstruction unit 52 uses the projection data corresponding to the X-ray images corrected by the second image correction unit 50 to reconstruct the second X-ray tomographic image at a cross section located at a given height of the subject 30 as does the first image reconstruction unit 42.

The selector 60 switches between the first X-ray tomographic image and the second X-ray tomographic image at a given timing according to the selection signal supplied from the controller 14 to output the selected X-ray tomographic image.

The X-ray tomographic image outputted from the selector 60 is displayed on the monitor 20. Upon a control by the controller 14, information on the display status of the X-ray tomographic image (information indicating which of the first and the second X-ray tomographic images is displayed) is displayed on the monitor 20 and an input screen for entering an instruction using the input unit 12 for selectively displaying the first X-ray tomographic image and the second X-ray tomographic image is also displayed on the monitor 20.

The X-ray tomographic image outputted from the selector 60 is supplied to the output unit 22, which, for example, prints out the X-ray tomographic image or allows digital image data of the X-ray tomographic image to be stored in a recording medium.

As described above, changing, as appropriate, corrections to be made on the X-ray images acquired by tomosynthesis imaging allows the imaging system 10 to perform only appropriate corrections as necessary. Therefore, an X-ray tomographic image well balanced in time required for correction and image quality can be provided.

The user of the imaging system 10 can know by referring to the X-ray tomographic image display status information whether the X-ray tomographic image displayed on the monitor 20 is the first X-ray tomographic image or the second X-ray tomographic image. The user can freely switch between the first X-ray tomographic image and the second X-ray tomographic image at any timing desired by issuing a switching instruction through the instruction input screen on the input unit 12.

The specific structure of each component of the X-ray imaging system of the invention is not limited in any manner and may be achieved by any of various means used to provide similar functions.

The present invention, described above in detail, is not limited in any manner to the above embodiments and various improvements and modifications may be made without departing from the spirit of the invention.

What is claimed is:

1. An X-ray imaging system comprising:
   an imaging unit for irradiating a subject with X ray at different angles while moving an X-ray source in one direction in tomosynthesis imaging, detecting the X ray with which the subject has been irradiated with a flat panel detector to acquire projection data of X-ray images taken at different angles; and
   an image processor for reconstructing a first X-ray tomographic image using projection data of the X-ray images acquired by the imaging unit,
   the image processor including:
   a correction decision unit for selecting, according to a given selection condition, one of previously provided different corrections to be performed on the projection data of the X-ray images acquired by the imaging unit;
   a first image correction unit for performing correction based upon the correction selected by the correction decision unit on the projection data of the X-ray images acquired by the imaging unit; and
   a first image reconstruction unit for reconstructing the first X-ray tomographic image using the projection data of the X-ray images corrected by the first image correction decision unit, wherein the image processor comprises:
- a second image correction unit for performing a previously provided correction on the projection data of the X-ray images acquired by the imaging unit;
- a second image reconstruction unit for reconstructing a second X-ray tomographic image using the projection data of the X-ray images corrected by the second image correction decision unit; and
- a selector for selectively outputting the first X-ray tomographic image reconstructed by the first image reconstruction unit and the second X-ray tomographic image reconstructed by the second image reconstruction unit at a given timing.

2. The X-ray imaging system according to claim 1, wherein the correction decision unit selects, according to the selection condition, one correction table from previously provided correction tables having corrections therein set out and adopts a correction that is set out in the selected correction table as a correction to be performed on each projection data of the X-ray images acquired by the imaging unit.

3. The X-ray imaging system according to claim 1, further comprising an imaging condition selection unit for selecting one or more imaging conditions from previously provided tomosynthesis imaging conditions and outputting the selected one or more imaging conditions as the selection condition.

4. The X-ray imaging system according to claim 3, wherein the imaging condition selection unit selects the one or more imaging conditions according to an instruction entered from outside.

5. The X-ray imaging system according to claim 3, wherein the predetermined tomosynthesis imaging conditions include one or more conditions selected from a number of images to be acquired, a dose of radiation, an imaging angle, imaging interval, a purpose of image acquisition, a site of a subject to be imaged, an imaging range, and an imaging environment.

6. The X-ray imaging system according to claim 1, wherein the correction decision unit determines not to correct the projection data of the X-ray images acquired by the imaging unit according to the selection conditions.

7. The X-ray imaging system according to claim 1, wherein the selector outputs the first X-ray tomographic image after the first image reconstruction unit completes reconstruction of the first X-ray tomographic image and outputs the second X-ray tomographic image after the second image reconstruction unit completes reconstruction of the second X-ray tomographic image.

8. The X-ray imaging system according to claim 7, wherein when a given time has elapsed after reconstruction of the second X-ray tomographic image is completed, the selector switches from the first X-ray tomographic image to the second X-ray tomographic image, and outputs the second X-ray tomographic image.

9. The X-ray imaging system according to claim 1, wherein after reconstruction of the second X-ray tomographic image is completed, the selector selectively outputs the first X-ray tomographic image and the second X-ray tomographic image according to an instruction entered from an outside.

10. The X-ray imaging system according to claim 1, wherein after the first image reconstruction unit completes reconstruction of the first X-ray tomographic image, the selector outputs the first X-ray tomographic image, and repeatedly switches from a reconstructed part of the second X-ray tomographic image to a corresponding part of the first X-ray tomographic image, each time the second image reconstruction unit reconstructs the part of the second X-ray tomographic image, until reconstruction of the second X-ray tomographic image is completed.

11. The X-ray imaging system according to claim 1, further comprising:
- an input unit for entering various instructions;
- a controller for controlling operations of the X-ray imaging system according to an instruction entered from the input unit; and
- a monitor for showing the X-ray tomographic images outputted from the selector;
- wherein the controller causes the monitor to indicate information on display status as to whether the first X-ray tomographic image is displayed or the second X-ray tomographic image is displayed.

12. The X-ray imaging system according to claim 11, wherein the controller causes the monitor to indicate an input screen for entering an instruction for selectively displaying the first X-ray tomographic image and the second X-ray tomographic image.

13. An X-ray imaging method, comprising the steps of:
- irradiating a subject with X ray at different angles while moving an X-ray source in one direction in tomosynthesis imaging, and detecting the X ray with which the subject has been irradiated with a flat panel detector to acquire projection data of X-ray images taken at different angles;
- selecting, according to a given selection condition, one of previously provided different corrections to be performed on the projection data of the acquired X-ray images;
- performing a first correction based upon the selected correction on the projection data of the acquired X-ray images;
- reconstructing a first X-ray tomographic image using the projection data of the X-ray images corrected according to the first correction;
- performing a predetermined second correction on the projection data of the acquired X-ray images;
- reconstructing a second X-ray tomographic image using the projection data of the X-ray images corrected according to the second correction; and
- selectively outputting the first X-ray tomographic image and the second X-ray tomographic image at a given timing.

14. A non-transitory computer-readable medium storing an X-ray imaging program for causing a computer to execute the steps of:
- irradiating a subject with at different angles while moving an X-ray source in one direction in tomosynthesis imaging, and detecting the X ray with which the subject has been irradiated with a flat panel detector to acquire projection data of X-ray images taken at different angles;
- selecting, according to a given selection condition, one of previously provided different corrections to be performed on the projection data of the acquired X-ray images;
- performing a first correction based upon the selected correction on the projection data of the acquired X-ray images;
- reconstructing a first X-ray tomographic image using the projection data of the X-ray images corrected according to the first correction;
- performing a predetermined second correction on the projection data of the acquired X-ray images;

reconstructing a second X-ray tomographic image using the projection data of the X-ray images corrected according to the second correction; and selectively outputting the first X-ray tomographic image and the second X-ray tomographic image at a given timing.

\* \* \* \* \*